United States Patent [19]
McMahon et al.

[11] Patent Number: 6,004,967
[45] Date of Patent: Dec. 21, 1999

[54] PSORIASIS TREATMENT WITH QUINAZOLINE COMPOUNDS

[75] Inventors: Gerald McMahon; Laura Shawver, both of San Francisco; Blair Narog, Mountain View; Peng Cho Tang, Moraga; Klaus Peter Hirth, San Francisco, all of Calif.

[73] Assignee: Sugen, Inc., Redwood City, Calif.

[21] Appl. No.: 08/927,442

[22] Filed: Sep. 11, 1997

Related U.S. Application Data

[60] Provisional application No. 60/026,067, Sep. 13, 1996, and provisional application No. 60/048,372, Jun. 3, 1997.

[51] Int. Cl.$^6$ .................................................. A61K 31/505
[52] U.S. Cl. ............................................................ 514/259
[58] Field of Search ............................................. 514/259

[56] References Cited

U.S. PATENT DOCUMENTS 5,457,105  10/1995  Barker ................................. 514/234.5

FOREIGN PATENT DOCUMENTS

| 0 566 226 A1 | 10/1993 | European Pat. Off. . |
|---|---|---|
| 92/20642 | 11/1992 | WIPO . |
| 95/03283 | 2/1995 | WIPO . |
| 96/09294 | 3/1996 | WIPO . |
| 96/27797 | 9/1996 | WIPO . |

OTHER PUBLICATIONS

Ben–Bassat, et al., "Tyrphostins Suppress the Growth of Psoriatic Keratinocytes" *Exper. Dermatol.,* 4(2):82–84 (1995).
Ben–Basset et al., "Inhibitors of Epidermal Growth Factor Receptor Kinase and Cyclin Dependent Kinase 2 Activation Induce Growth Arrest, Differentiation, and Apoptosis of Human Papilloma Virus 16–Immortalized Human Keratinocytes", *Cancer Research,* vol. 57:3741–3750 (1997).
Broker and Botchan, "Papillomaviruses: Retrospectives and Prospectives," *Cancer Cells–DNA Tumor Viruses,* New York: Cold Spring Harbor Laboratory (1986).
Bronaugh, "Preparation of Biological Membranes", In: *Methods for Skin Absorption,* pp. 61–66. Ed. Barbara Kempanien and William G. Reifenrath, CRC Press (1990).
Decker and Lohmann–Matthes, "A Quick and Simple method for the Quantitation of Lactate Dehydrogenase Release in Measurements of Cellular Cytotoxicity and Tumor Necrosis Factor (TNF) Activity", *J. Immunol. Methods* 15:61–69 (1988).
Durst, et al., "Molecular and cytogenetic analysis of immortalized human primary keratinocytes obtained after transfection with human papillomavirus type 16 DNA," *Oncogene,* 1:251–256 (1987).
Dvir et al., "The Inhibition of EGF–dependent Proliferation of Keratinocytes by Tyrphostin Tyrosine Kinase Blockers," *J. Cell Biol.* 113:857–865 (1991).
Elder, et al., "Overexpression of Transforming Growth Factor α in Psoriatic Epidermis," *Science,* 243:811–814 (1989).

Ellis et al., "Melanoma, Growth Factors, Acanthosis Nigricans, the Sign of Leser–Trelat, and Multiple Acrochordons," *N. Engl. J. Med.* 317:1582–1587 (1987).
Fendley et al., "Characterization of Murine Monoclonal Antibodies Reactive to Either the Human Epidermal Growth Factor Receptor or HER2/neu Gene Product," *Cancer Research* 50:1550–1558 (1990).
Gazit, et al., "Tyrophostins IV–Highly Potent Inhibitors of EGF Receptor Kinase. Structure–Activity Relationship Study of 4–Anilidoquinazolines," *Biorg. Med. Chem.* 4:1203–1207 (1996).
Gottlieb, et al., "Detection of Transforming Growth Factor α In Normal, Malignant, and Hyperproliferative Human Keratinocytes," *J. Exp. Med.,* 167:670–675 (1988).
Green et al., "Differences in Human Skin Between the Epidermal Growth Factor Receptor Distribution Detected by EGF Binding and Monoclonal Antibody Recognition," *J. Invest. Dermatol.* 85:239–245 (1985).
Grossman, et al., "Interleukin 6 is expressed in high levels in psoriatic skin and stimulates proliferation of cultured human keratinocytes," *Proc. Natl Acad Sci USA,* 86:6367–6371 (1989).
Hagedorn, M. and T. Baukrecht, "Evidence of EGF like Factors (EGF–F) in Different Skin Tumors," *Z. Hautkr* 65(6):575–577 (1990) GERMAN.
Kawamoto, T., et al. "Relation of Epidermal Growth Factor Receptor Concentration to Growth of Human Epidermoid Carcinoma A431 Cells," *J. Biol. Chem.* 259(12):7761–7766 (1984).
Korzeniewski and Callewaert, "An Enzyme–Release Assay for Natural Cytotoxicity," *J. Immunol. Methods* 64:313–320 (1983).
Krane, et al., "Synergistic Effects of Epidermal Growth Factor (EGF) and Insulin–Like Growth Factor I/Somatomedin C (IGF–I) on Keratinocyte Proliferation may Be Mediated by IGF–I Transmodulation of the EGF Receptor," *J. Invest. Dermatol.,* 96:419–424 (1991).
Krane, et al., "The Insulin–like Growth Factor I Receptor is Overexpressed in Psoriatic Epidermis, but Is Differentially Regulated from the Epidermal Growth Factor Receptor," *J. Exp. Med.,* 175:1081–1090 (1992).
Krueger, et al., "Role of Growth Factors, Cytokines, and Their Receptors in the Pathogenesis of Psoriasis," *J. Invest. Dermatol.,* 94:1355–1405 (1990).
Kumar et al., "A Simple Microwave Technique for the Separation of Epidermis and Dermis in Skin Uptake Studies," *Pharmaceutical Res.* 6:740–741 (1989).
Levitzki, "Signal–Transduction Therapy", *Eur. J. Biochem.,* vol. 226, No. 1:1–13 (1994).
Levitzki, "Receptor Activation by Antigens, Cytokines, Hormones and Growth Factors", *Annals of the New York Academy of Sciences,* vol. 766:363–368 (1995).

(List continued on next page.)

*Primary Examiner*—Raymond Henley, III
*Attorney, Agent, or Firm*—Lyon & Lyon LLP

[57] ABSTRACT

This invention is directed to methods and compositions for treating hyperproliferative skin disorders utilizing a quinazoline derivative as an active ingredient.

8 Claims, No Drawings

OTHER PUBLICATIONS

Mossman, "Rapid Colorimetric Assay for Cellular Growth and Survival: Application to Proliferation and Cytotoxicity Assays," *J. Immunol. Methods* 65:55–63 (1983).

Nanney et al., "Comparison of Epidermal Growth Factor Binding and Receptor Distribution in Normal Human Epidermis and Epidermal Appendages," *J. Invest. Dermatol.* 83(5):385–393, 1984; Green et al., *J. Invest. Dermatol.* 85:239–245 (1985).

Nanney, et al., "Altered [$^{125}$I] Epidermal Growth Factor Binding and Receptor Distribution in Psoriasis," *J. Invest. Dermatol.*, 86(3):260–265 (1986).

Nanney, et al., "Modulation of Epidermal Growth Factor Receptors in Psoriatic Lesions During Treatment with Topical EGF," *J. Invest. Dermatol.*, 98:296–301 (1992).

Parkin, et al., "Estimates of the Worldwide Frequency of Sixteen Major Cancers in 1980," *Cancer*, 41:184–187 (1988).

Pfister, "Biology and Biochemistry of Papillomaviruses," *Rev. Phys. Biochem. Pharmacol.*, 99:111–181 (1984).

Traxler et al., "4–Phenylamino(pyrrolopyrimidines): Potent and Selective, ATP Site Directed Inhibitors of the EGF–Receptor Protein Tyrosine Kinase", *J. Med. Chem*, vol. 39, No. 12:2285–2292 (1996).

Ullrich and Schlessinger, "Signal Transduction by Receptors with Tyrosine Kinase Activity," *Cell* 61:203–212 (1990).

Vassar, et al., "Transgenic mice provide new insights into the role of TGF–α during epidermal development and differentiation," *Genes and Develop.*, 5:714–727 (1991).

Weinstein, et al., "Cell Kinetic Basis for Pathophysiology of Psoriasis," *J. Invest. Dermatol.*, 85:579 (1985).

Wright and Camplejohn, Eds., *Psoriasis: Cell Proliferation*, (Churchill Livingstone, Edinburgh, 1983), pp. 147–295.

Zur Hausen, "Herpes Simplex Virus in Human Genital Cancer," *Int. Rev. Exp. Path.*, 25:307–326 (1983).

Bridges, et al., "Tyrosine Kinase Inhibitors. 8. An Unusually Step Structure–Activity Relationship for Analogues of 4–(3–Bromoanilino)–6,7–Dimethoxyquinazoline (PD153035), a Potent Inhibitor of the Epidermal Growth Factor Receptor," *J. Med. Chem.* 39:267–76 (1996).

PSORIASIS TREATMENT WITH QUINAZOLINE COMPOUNDS

RELATED APPLICATIONS

This application claims priority benefits of the following provisional applications: Serial No. 60/026,067, filed Sep. 13, 1996, and Serial No. 60/048,372, filed Jun. 3, 1997. The content of the above identified provisional applications is incorporated by reference herein in their entirety, including drawings, tables, formulas and sequences.

FIELD OF THE INVENTION

The present invention relates to methods, compositions and formulations for treating skin diseases and disorders characterized by keratinocyte hyperproliferation.

BACKGROUND OF THE INVENTION

Approximately four and one half million people in the U.S. are afflicted with psoriasis. Psoriasis is a skin disease often confined to localized areas of skin. It is typified by dry, scaly skin, abnormal thickening of epidermis, and rapid cell turnover in the skin. Psoriasis can be exacerbated by external factors including sun exposure, viral infections, and corticosteroid or beta-blocker use. Histologically, it is characterized by abnormalities including keratinocyte hyperplasia, abnormal differentiation sequence of keratinocytes in affected epidermis, and accumulation of leukocytes within the epidermis (Wright and Camplejohn, Eds., *Psoriasis: Cell Proliferation*, (Churchill Livingstone, Edinburgh, 1983), pp. 147–295; Weinstein, et al., *J. Invest. Dermatol.*, 85:579, 1985).

Other skin disorders characterized by skin cell hyperproliferation include actinic keratoses, seborrheic keratoses and skin cancers such as basal cell carcinoma.

Infection with papilloma viruses also causes skin cell hyperproliferation (Zur Hausen, *Int. Rev. Exp. Path.*, 25:307–326 (1983); Pfister, *Rev. Phys. Biochem. Pharmacol.*, 99:111–181 (1984). Infection of cervix by certain papilloma viruses has been strongly linked to a majority of cervical cancers, the second largest cause of cancer deaths in women worldwide (Parkin, et al., *Cancer*, 41:184–187 (1988); Durst, et al., *Oncogene*, 1:251–256 (1987); Broker and Botchan, *Cancer Cells—DNA Tumor Viruses*, New York: Cold Spring Harbor Laboratory, 1986).

Keratinocyte hyperplasia in psoriasis is linked to overproduction of cytokines such as TGα and interleukin-6 (IL-6) and overexpression of epidermal growth factor receptor (EGF-R) in affected skin (Krueger, et al., *J. Invest. Dermatol.*, 94:1355–1405, 1990). EGF-R is a 180-kD cell-surface receptor whose activity is regulated by both EGF and TGFα. In psoriasis vulgaris, EGF-R persists throughout the epidermis from the basal layers to the stratum corneum. Such persistent EGF-R has been shown to be biologically active in vivo in nude mice (Nanney, et al., *J. Invest. Dermatol.*, 98:296–301, 1992).

Suggested treatment for psoriasis includes direct inhibition of keratinocyte growth and inhibition of activated lymphocyte proliferation (Dvir et al., *J. Cell Biol.* 113:857–865, 1991). Many topical products currently available are irritating, messy or simply ineffective. Topical steroids account for 90% of the psoriasis market in the United States and have many side effects including cutaneous atrophy, telangiectasia, formation of striae and tachyphylaxis.

SUMMARY OF THE INVENTION

Epidermal hyperproliferation and angiogenesis are hallmarks of psoriasis. In the scope of the present invention it has been found that quinazoline derivatives such as 4-(3-Bromophenylamino)-6,7-dimethoxyquinazoline, 4-(3-Chlorophenylamino)-6,7-dimethoxyquinazoline, 4-(3-Chlorophenylamino)-6-methylquinazoline, 4-[3-(trifluoromethyl)phenylamino]-6,7-dimethoxyquinazoline, 4-(3-Cyanophenylamino)-6,7-dimethoxyquinazoline, 4-[3-(trifluoromethyl)phenylamino]-6-methylquinazoline, or a pharmaceutically acceptable salt thereof (identified as A1, A2, A3, A4, A5, and A6 in Table 1) have the properties of inhibiting or reducing the EGF-R tyrosine kinase activity and skin cell hyperproliferation. The administration of an effective amount of an above mentioned compound to a patient suffering from psoriasis or other hyperproliferative skin diseases will be able to inhibit the abnormal proliferation of skin cells, and decrease cornification, scaling or uneven thickness and other undesirable symptoms of psoriasis. The present invention is based on the aforementioned finding and is accordingly concerned with the novel use of the compounds in the treatment or prevention of skin diseases and disorders characterized by hyperproliferation.

Therefore, the present invention relates to methods and compositions for the treatment or prevention of hyperproliferative skin disorders, including, but not limited to, psoriasis (e.g. psoriasis vulgaris, psoriasis pustulosa, psoriasis erythrodermica, psoriasis arthropathica, parapsoriasis, palmoplantar pustulosis) and skin cancer. In preferred embodiments, a host (e.g. a mammal or human) is administered a composition containing a pharmaceutically effective amount of a compound of Formula I, such as A1, A2, A3, A4, A5, A6, or a pharmaceutically acceptable salt thereof. The compositions of this invention cure, reduce or prevent keratinocyte hyperproliferation or skin lesions in the host. A preferred drug is highly potent and selective with low toxicity.

Formula I

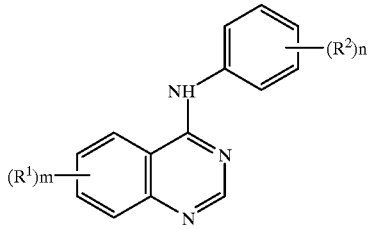

In Formula I, m is 1, 2 or 3 and n is 1 or 2.

Each $R^1$ is independently selected from the group consisting of hydroxy, amino, carboxy, carbamoyl, ureido, (1-6C)alkoxycarbonyl, N-(1-6C)alkylcarbamoyl, N,N-di-[(1-6C)alkyl]carbamoyl, hydroxyamino, (1-6C) alkoxyamino, (2-6C)alkanoyloxyamino, trifluoromethoxy, (1-6C)alkyl, (1-6C)alkoxy, (1-3C)alkylenedioxy, (1-6C) alkylamino, di-[(1-6C)alkyl]amino, pyrrolidin-1-yl, piperidino, morpholino, piperazin-1-yl, 4-(1-6C) alkylpiperazin-1-yl, (1-6C)alkylthio, (1-6C)alkylsulphinyl, (1-6C)alkylsulphonyl, halogen-(1-6C)alkyl (other than trifluoromethyl), hydroxy-(1-6C)alkyl, (2-6C)alkanoyloxy-(1-6C)alkyl, (1-6C)alkoxy-(1-6C)alkyl, carboxy-(1-6C) alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, amino-(1-6C) alkyl, (1-6C)alkylamino-(1-6C)alkyl, di-[-(1-6C)alkyl] amino-(1-6C)alkyl, piperidino-(1-6C)alkyl, morpholino-(1-6C)alkyl, piperazin-1-yl-(1-6C)alkyl, 4-(1-6C) alkylpiperazin-1-yl-(1-6C)alkyl, hydroxy-(2-6C)alkoxy- (1–6C)alkyl, (1–6C)alkoxy-)2–6C)alkoxy-(1–6C)alkyl, hydroxy-(2–6C)alkylamino-(1–6C)alkyl, (1–6C)alkoxy-(2–6C)alkylamino-(1–6C)alkyl, (1–6C)alkylthio-(1–6C) alkyl, hydroxy-(2–6C)alkylthio-(1–6C)alkyl, (1–6C) alkoxy-(2–6C)alkylthio-(1–6C)alkyl, phenoxy-(1–6C)alkyl, anilino-(1–6C)alkyl, phenylthio-(1–6C)alkyl, cyano-(1–6C) alkyl, halogen-(2–6C)alkoxy, hydroxy-(2–6C)alkoxy, (2–6C)alkanoyloxy-(2–6C)alkoxy, (1–6C)alkoxy-(2–6C) alkoxy, carboxy-(1–6C)alkoxy, (1–6C)alkoxycarbonyl-(1–6C)alkoxy, carbamoyl-(1–6C)alkoxy, N-(1–6C)alkoxy, amino-(2–6C)alkoxy, (1–6C)alkylamino-(2–6C)alkoxy, di-[(1–6C)alkyl]amino-(2–6C)alkoxy, (2–6C)alkanoyloxy, hydroxy-(2–6C)alkanoyloxy, (1–6C)alkoxy-(2–6C) alkanoyloxy, phenyl-(1–6C)alkoxy, phenoxy-(2–6C)alkoxy, anilino-(2–6C)alkoxy, phenylthio-(2–6C)alkoxy, piperidino-(2–6C)alkoxy, morpholino-(2–6C) alkoxy, piperazin-1-yl-(2–6C)alkoxy, 4-(1–6C)alkylpiperazin-1-yl-(2–6C)alkoxy, halogen-(2–6C)alkylamino, hydroxy-(2–6C) alkylamino, (2–6C)alkanoyloxy-(2–6C)alkylamino, (1–6C) alkoxy-(2–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C) alkylamino, N,N-di-[(1–6C)alkyl]carbamoyl-(1–6C) alkylamino, amino-(2–6C)alkylamino, (1–6C)alkylamino-(2–6C) alkylamino, di-[(1–6C)alkyl]amino-(2–6C) alkylamino, phenyl-(1–6C) alkylamino, phenoxy-(2–6C) alkylamino, anilino-(2–6C) alkylamino, phenylthio-(2–6C) alkylamino, (2–6C)alkanoylamino, (1–6C) alkoxycarbonylamino, (1–6C) alkylsulphonylamino, benzamido, benzenesulphonamido, 3-phenylureido, 2-oxopyrrolidin-1-yl, 2,5-dioxopyrrolidin-1-yl, halogen-(2–6C)alkanoylamino, hydroxy-(2–6C)alkanoylamino, (1–6C)alkoxy-(2–6C)alkanoylamino, carboxy-(2–6C) alkanoylamino, (1–6C)alkoxycarbonyl-(2–6C) alkanoylamino, carbamoyl-(2–6C) alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C) alkanoylamino and di-[(1–6C)alkyl]amino-(2–6C) alkanoylamino, and wherein said benzamido or benzenesulphonamido substituent or any anilino, phenoxy or phenyl group in a $R^1$ substituent may optionally bear one or two halogen, (1–6C)alkyl or (1–6C)alkoxy substituents.

Each $R^2$ of formula I is independently selected from the group consisting of hydrogen, hydroxy, halogen, trifluoromethyl, amino, nitro, cyano, (1–6C)alkyl, (1–6C) alkoxy, cyclo[(1–3C)alkenedioxy], (1–6C)alkylamino, di-[(1–6C)alkyl]amino, (1–6C)alkylthio, (1–6C)alkylsulphinyl and (1–6C)alkylsulphonyl.

In a preferred embodiment, each $R^1$ is independently selected from the group consisting of hydroxy, amino, ureido, methoxycarbonyl, ethoxycarbonyl, hydroxyamino, trifluoromethoxy, methyl, ethyl methoxy, ethoxy, propoxy, isopropoxy, butoxy, methylenedioxy, ethylenedioxy, methylamino, ethylamino, dimethylamino, diethylamino, piperidino, morpholino, mehtylthio, ethylthio, bromomethyl, dibromomethyl, methoxymethyl, piperidinomethyl, morpholinomethyl, piperazin-1-ylmethyl, methoxyethoxymethyl, methylthiomethyl, 2-hydroxyethylthiomethyl, anilinomethyl, phenylthiomethyl, cyanomethyl, 2-bromoethoxy, 2-hydroxyethoxy, 3-hydroxypropoxy, 2-methoxyethoxy, 2-ethoxyethoxy, 3-methoxypropoxy, 3-ethoxypropoxy, methoxycarbonylmethoxy, ethoxycarbonylmethoxy, carbamoylmethoxy, 2-dimethylaminoethoxy, 2-diethylaminoethoxy, 2-methoxyacetoxy, benzyloxy, 2-anilinoethoxy, 2-peperidinoethoxy, 2-morpholinoethoxy, 2-(piperazin-1-yl)ethoxy, 2-hydroxyethylamino, 3-hydroxypropylamino, 2-methoxyethylamino, 2-ethoxyethylamino, 3-methoxypropylamino, 3-ethoxypropylamino, 2-dimethylaminoethylamino, 2-diethylaminoethylamino, 3-dimethylaminopropylaminno, 3-diethylaminopropylamino, acetamido, propionamido, benzamido, 3-phenylureido, 2-chloroacetamido, 2-oxopyrrolidin-1-yl, 2-hydroxyacetamido, 2-methoxyacetamido and 2-ethoxyacetamido. In addition, each $R^2$ is independently selected from the group consisting of hydrogen, fluoro, chloro, bromo, trifluoromethyl, nitro, cyano, methyl and ethyl.

In a further preferred embodiment, $(R^1)_m$ is selected from the group consisting of 6-hydroxy, 7-hydroxy, 6,7-dihydroxy, 6-amino, 7-amino, 6-ureido, 6-trifluoromethoxy, 6-methyl, 6,7-dimethyl, 6-methoxy, 7-methoxy, 6,7-dimethoxy, 6,7-diethoxy, 6-hydroxy-7-methoxy, 7-hydroxy-6-methoxy, 6-amino-7-methoxy, 6-amino-7-methylthio, 5-amino-6,7-dimethoxy, 6-methoxy-7-isopropoxy, 6,7-methylenedioxy, 6,7-ethylenedioxy, 6-methylamino, 7-methylamino, 6-dimethyiamino, 6-amino-7-methylamino, 6-methoxymethyl, 6-bromomethyl, 6-(2-methoxyethoxymethyl), 6-cyanomethyl, 6-methylthiomethyl, 6-phenylthiomethyl, 7-(2-hydroxyethoxy)-6-methoxy, 6,7-di-(2-hydroxyethoxy), 6-(2-bromoethoxy), 6-(2-methoxyethoxy), 6-methoxy-7-(2-methoxyethoxy), 6,7-di-(2-methoxyethoxy), 7-(2-bromoethoxy)-6-methoxy, 7-benzyloxy-6-methoxy, 6-(2-methoxyethylamino), 6-acetamido, 6-benzamido, 6-(2-chloroacetamido), 6-(2-methoxyacetamido) and 7-(2-methoxyacetamido). In addition, $(R^2)_n$ is selected from the group consisting of hydrogen, 4'-fluoro, 3'-chloro, 3'-bromo, 3',4'-dichloro, 4'-fluoro-3'-chloro, 3'-trifluoromethyl, 4'-fluoro-3'-trifluoromethyl, 3'-nitro, 3'-nitro-4'-chloro, 3'-nitro-4'-flouro and 3'-methyl groups.

An "alkyl" group refers to a saturated aliphatic hydrocarbon, including straight-chain, branched-chain, and cyclic alkyl groups. Preferably, the alkyl group has 1 to 12 carbons. More preferably, it is a lower alkyl of from 1 to 7 carbons, more preferably 1 to 4 carbons, such as, e.g., methyl, ethyl, n-propyl, iso-propyl, n-butyl, sec-butyl, iso-butyl, tert-butyl, and 2-methylpentyl. The alkyl group may be substituted or unsubstituted. When substituted the substituted group(s) is preferably hydroxyl, cyano, alkoxy, =O, =S, $NO_2$, $N(CH_3)_2$, amino, or SH.

An "alkoxy" group refers to an "-O-alkyl" group, where "alkyl" is defined as described above, such as methoxy, ethoxy, n-propoxy, iso-propoxy, n-butoxy, sec-butoxy, iso-butoxy, tert-butoxy, trifluoromethoxy, 3-hydroxyhexyloxy, 2-carboxypropyloxy, 2-fluoroethoxy, carboxymethoxy and cyanobutyloxy and the like.

An "alkenyl" group refers to an unsaturated hydrocarbon group containing at least one carbon-carbon double bond, including straight-chain, branched-chain, and cyclic groups. Preferably, the alkenyl group has 1 to 12 carbons. More preferably it is a lower alkenyl of from 2 to 7 carbons, more preferably 2 to 4 carbons. The alkenyl group may be substituted or unsubstituted. When substituted the substituted group(s) is preferably hydroxyl, cyano, alkoxy, =O, =S, $No_s$, halogen, $N(CH_3)_2$, amino, or SH. An "alkynyl" group refers to an unsaturated hydrocarbon group containing at least one carbon-carbon triple bond, including straight-chain, branched-chain, and cyclic groups. Preferably, the alkynyl group has 2 to 12 carbons. More preferably, it is lower alkynyl of from 2 to 7 carbons, more preferably 2 to 4 carbons. The alkynyl group may be substituted or unsubstituted. When substituted the substituted group(s) is preferably hydroxyl, cyano, alkoxy, =O, =S, $No_s$, $N(CH_3)_2$, amino or SH.

A "heterocycle" denotes a chain of carbon and at least one non-carbon atoms which together form one or more aromatic or non-aromatic rings having preferably between about 5–14 atoms, such as, e.g., furyl, thienyl, imidazolyl, indolyl, pyridinyl, thiadiazolyl, thiazolyl, piperazinyl, dibenzfuranyl, dibenzthienyl. These rings may be optionally substituted with one or more functional groups which are attached commonly to such rings, such as, e.g., hydroxyl, bromo, fluoro, chloro, iodo, mercapto or thio, cyano, cyanoamido, alkylthio, heterocycle, aryl, heteroaryl, carboxyl, oxo, alkoxycarbonyl, alkyl, alkenyl, nitro, amino, alkoxyl, amido, and the like to form rings such as, e.g., 2-aminothiazol-4-yl, 2-amino-5-chlorothiazol-4-yl, 2-amino-thiadiazol-4-yl, 2,3-dioxopiperazinyl, 4-alkylpiperazinyl, 2-iodo-3-dibenzfuranyl and 3-hydroxy-4-dibenzthienyl and the like.

An "aryl" group refers to an aromatic group which has at least one ring having a conjugated pi electron system and includes carbocyclic aryl, heterocyclic aryl and biaryl groups, all of which may be optionally substituted. Preferably, the aryl is a substituted or unsubstituted phenyl or pyridyl. Preferred aryl substituent(s) are halogen, trihalomethyl, hydroxyl, SH, OH, $NO_2$, amine, thioether, cyano, alkoxy, alkyl, and amino groups.

An "alkylaryl" group refers to an alkyl as described above covalently joined to an aryl group as described above. Preferably, the alkyl is a lower alkyl.

"Carbocyclic aryl" groups are groups wherein the ring atoms on the aromatic ring are all carbon atoms. The carbon atoms are optionally substituted.

"Heterocyclic aryl" groups are groups having from 1 to 3 heteroatoms as ring atoms in the aromatic ring and the remainder of the ring atoms are carbon atoms. Suitable heteroatoms include oxygen, sulfur, and nitrogen. The heterocyclic aryl groups of this invention include, but are not limited to, furanyl, thienyl, pyridyl, pyrrolyl, N-lower alkyl pyrrolo, pyrimidyl, pyrazinyl, imidazolyl and the like, all optionally substituted.

An "aryloxy" denotes -OAr, where Ar is an aryl group as defined above.

An "aralkyl" denotes -RAr, where R is alkyl and Ar is aryl, both as defined above.

An "amide" refers to an —C(O)—NH—R, where R is either alkyl, aryl, alkylaryl or hydrogen.

An "amine" refers to a —N(R")R'", where R" and R'", is independently either hydrogen, alkyl, aryl, or alkylaryl, provided that R" and R'" are not both hydrogen.

An "amino" denotes the group NRR', where R and R' may independently be alkyl, aryl or acyl as defined above, or hydrogen.

A "cyanoamido" refers to the group —NH—C≡N.

In addition to psoriasis, other diseases or pathological conditions characterized by hyperproliferation and/or EGF-R overexpression and hyperactivity can be treated with the above-described compositions. These diseases and pathological conditions include, but are not limited to, keratinocyte proliferation and skin lesions caused or induced by Papilloma virus infection, seborrheic keratoses, acanthosis nigricans, ichthyosis (e.g. ichthyosis vulgaris and congenital ichthyoses), keratodermias, genodermatoses with pathological cornification disorders (e.g. Darier's disease), further lichen ruber planus, pityriasis rubra pilaris, and skin cancers such as basal cell carcinoma, squamous cell carcinoma and melanoma.

By "pharmaceutically effective" is meant the ability to cure, reduce or prevent one or more clinical symptoms of keratinocyte hyperproliferation, including, but not limited to, cornification, scaling, uneven thickness, inflammation, and rapid cell turnover in the skin.

The composition containing a pharmaceutically effective ingredient may be administered topically or systemically. In a preferred embodiment, it is administered topically to an affected skin area.

In a preferred embodiment, A1 or its pharmaceutically acceptable salts are used in the composition. Such a composition is especially suitable for topical treatment vis-a-vis systemic treatment of skin conditions because of the following properties of A1: (1) low toxicity, (2) short plasma half-life, and (3) relative high solubility in nonirritant solvents among anticancer compounds. Low toxicity is a desirable feature for a drug used to treat a non-life threatening disease. Short plasma half-life helps to keep the drug's therapeutic effects localized to where it is topically applied. Formulations with nonirritant solvents alleviate the suffering of patients who have to use the drug repeatedly to receive the desired therapeutic effects.

In another aspect, this invention features a pharmaceutical composition for the treatment of a hyperproliferative skin disorder containing a pharmaceutically effective amount of a compound selected from the group consisting of A1, A2, A3, A4, A5, A6 and their pharmaceutically acceptable salts; and a pharmaceutically acceptable carrier. In a preferred embodiment, the pharmaceutical composition is for topical application to a host. In another preferred embodiment, the compound is selected from the group consisting of A1 and its pharmaceutically acceptable salts.

The composition may be in a unit dosage form or a multiple use dosage form. In a preferred embodiment, the composition is held within a container which includes a label stating to the effect that the composition is approved by the FDA in the United States (or an equivalent regulatory agency in a foreign country) for treating a hyperproliferative skin disorder such as psoriasis (e.g. psoriasis vulgaris, psoriasis pustulosa, psoriasis erythrodermica, psoriasis arthropathica, parapsoriasis, palmoplantar pustulosis), skin lesions caused by Papilloma virus infection, seborrheic keratoses, acanthosis nigricans, ichthyosis (e.g. ichthyosis vulgaris and congenital ichthyoses), keratodermias, genodermatoses with pathological cornification disorders (e.g. Darier's disease), further lichen ruber planus, pityriasis rubra pilaris, or a skin cancer such as basal cell carcinoma, squamous cell carcinoma or melanoma. Such a container provides a therapeutically effective amount of the active ingredient to be administered to a host.

In yet another aspect, this invention features a method of making a composition for the treatment of a hyperproliferative skin disorder by providing a pharmaceutically effective amount of a compound selected from the group consisting of A1, A2, A3, A4, A5, A6 and their pharmaceutically acceptable salts, and admixing the compound with a pharmaceutically acceptable carrier. Preferably, the composition is further packaged into a container in a unit dosage or a multiple use dosage.

This invention also features a method of preparing a compound for treating a hyperproliferative skin disorder by providing a plurality of compounds of Formula I, testing these compounds' ability to specifically inhibit EGF-R tyrosine kinase activity using the assays deseribed and disclosed in this application (such as those in Examples 1–8), and selecting those with activity in the range of A1, A2, A3, A4, A5, and A6. A pharmaceutically effective amount of such compounds is further packaged in a container with a pharmaceutically acceptable carrier.

Other features and advantages of the invention will be apparent from the following detailed description of the invention, and from the claims.

DETAILED DESCRIPTION OF THE PREFERRED EMBODIMENTS

I. Quinazoline Derivatives of this Invention Target EGF-R for Therapeutic Intervention of Hyperproliferative Skin Diseases This invention concerns treating or preventing psoriasis and other conditions characterized by keratinocyte hyperproliferation by inhibiting or reducing EGF-R activity with quinazoline derivatives.

Psoriatic epidermis is associated with altered protein tyrosine kinase, phospholipase C (PLC) and protein kinase C (PKC) activities, all of which are changed by chronic EGF-R activation. Growth factors, cytokines and their receptors are involved with the disease process of psoriasis (Krueger, et al., *J. Invest. Dermatol.*, 94:1355–1405, 1990). Among them, EGF-R plays a crucial role in the hyperproliferation of keratinocytes in psoriatic lesions.

EGF-R is overexpressed in psoriatic keratinocytes (Nanney, et al., *J. Invest. Dermatol.*, 86:260–265, 1986). The normal basilar distribution of EGF receptors in epidermal keratinocytes is markedly altered in psoriasis vulgaris where they are also observed in the upper keratinocyte compartment (Nanney et al., *J. Invest. Dermatol.* 83:385–393, 1984; Green et al., *J. Invest. Dermatol.* 85:239–245, 1985). In a study on benign epidermal dermatoses, EGF receptor expression throughout the epidermis returned to a basal layer distribution when the lesion resolved (Ellis et al., *N. Engl. J. Med.* 317:1582–1587, 1987).

Psoriatic keratinocytes persistently secrete TGFα due to the overexpression of the TGFα gene (Gottlieb, et al., *J. Exp. Med.*, 167:670–675, 1988; Elder, et al., *Science*, 243:811–814, 1989; Vassar, et al., *Genes and Develop.*, 5:714–727, 1991). TGFα overexpression causes enhanced autocrine stimulation of the keratinocyte EGF-R (Grossman, et al., *Proc. Natl Acad Sci USA*, 86:6367–6371, 1989). IGF-1 receptor is also overexpressed in the psoriatic epidermis (Krane, et al., *J. Invest. Dermatol.*, 96:419–424, 1991; Krane, et al., *J. Exp. Med.*, 175:1081–1090, 1992). Activation by IGF-1 stimulates the synthesis of EGF-R and thus amplifies the effect of the EGF-R/TGFα autocrine loop. The finding that transgenic mice overexpressing TGFα in their skin develop lesions (Vassar, et al., *Genes and Develop.*, 5:714–727, 1991) supports the crucial role of EGF-R in the pathogenesis of the disease.

An EGF-R has three functional domains: an extracellular ligand binding domain, a transmembrane domain and a cytoplasmic domain capable of phosphorylating tyrosine residues. Ligand binding to the extracellular ligand binding domain of membrane-bound EGF-R induces the formation of receptor dimers and allosteric changes that activate the intracellular kinase domain to result in the phosphorylation (autophosphorylation and/or transphosphorylation) of tyrosine residues. The phospho-tyrosine residues of the cytoplasmic domains of EGF-R then interact with a host of cytoplasmic signaling molecules to activate signal transduction pathways (Ullrich and Schlessinger, *Cell* 61:203–212, 1990). During mitogenic activation of cells, the tyrosine kinase activity of EGF-R results in an increased activity of phospholipase C (PLC). The activation of EGF-R also results in the activation of protein kinase C (PKC), increased calcium uptake, and hydrolysis of membrane lipids to yield diacylglycerols (DAG) and inositol-triphosphate (IP3).

In psoriasis, hyperproliferation of keratinocytes is driven mainly by EGF-R and its ligands (Elder, et al., *Science*, 243:670–675, 1989). Some EGF-R blockers arrest the growth of psoriatic keratinocytes and are considered for clinical use (Ben-Bassat, et al., *Exper. Dermatol.*, 4(2):82–84, 1995). Tyrosine kinase blockers of the tyrphostin family have been shown to block the proliferation of psoriatic keratinocytes grown in culture (Dvir, et al., *J. Cell Biol.*, 113:857–865, 1991; Ben-Bassat, et al., *Exp. Dermatol.*, 4:82–88, 1995). Tyrphostins inhibit EGF-R autophosphorylation and EGF-dependent tyrosine phosphorylation of intracellular target proteins in keratinocytes.

Skin cancers have also been associated with the expression of EGF-R ligands and anti-EGF-R antibodies have been shown to inhibit the growth of a skin cancer cell line expressing EGF-R. (See Hagedorn, M. and T. Baukrecht, *Z. Hautkr* 65(6):575–577, 1990; Kawamoto, T., et al. *J. Biol. Chem.* 259(12):7761–7766, 1984).

The present application shows that quinazoline derivatives of this invention, i.e., A1, A2, A3, A4, A5 and A6, are able to inhibit EGF-stimulated EGF-R phosphorylation. These compounds also are capable of inhibiting EGF-mediated skin cell growth in vitro and psoriatic skin cell proliferation in vitro. Specifically, A1 potently inhibited ligand-induced autophosphorylation of the EGF receptor, and downstream signal transduction events, including DNA replication and cell cycle progression. The compound is specific for the EGF receptor, since it displayed little or no activity against unrelated receptor tyrosine kinases such as the receptors for platelet-derived growth factor or insulin-like growth factor-1. A1 was shown to block EGF receptor-dependent growth of tumor cells and fibroblasts engineered to overexpress EGF receptor. At micromolar concentrations, A1 was shown to inhibit the proliferation of keratinocytes isolated from psoriatic lesions. In skin penetration studies, radiolabelled compound penetrated human cadaver skin, reaching biologically effective concentrations in the epidermis within a 24-hour period.

II. Identification and Preparation of Compound

The chemical structures of A1, A2, A3, A4, A6 and A5 are shown below in Table 1. Methods for preparing these compounds can be found in U.S. Pat. No. 5,457,105 issued Oct. 10, 1995 and PCT publication WO 95/03283 published Feb. 2, 1995, the totality of which is incorporated by reference herein.

In an example, A1 was prepared essentially as described in Barker, AJ. European Patent Application 0 566 226 A1, Oct. 20, 1993; and Gazit et al., *Bioorg. Med. Chem.* 4:1203–1207, 1996. Briefly, methyl 2-amino-4,5-dimethoxybenzoate was treated with formamide at 180° C. The reaction was cooled and diluted with water. The precipitate was collected by filtration, washed with water and dried to give 6,7-dimethoxyquinazolone, which was treated with thionyl chloride and dimethylformamide at reflux, concentrated, and stirred with sodium bicarbonate solution. The resulting solid was collected and crystallized from hexane to give 4-chloro-6,7-dimethoxyquinazoline, which was refluxed with 3-bromoaniline in ethanol, cooled, treated with 1 normal NaOH and the resulting solid collected by filtration to yield 4-(3-bromophenylamino)-6,7-dimethoxyquinazoline (A1).

III. Treatment Indications

The above identified compounds may be used to treat skin diseases or pathological conditions in mammals, especially in humans.

The hyperproliferative diseases which cause abnormal scaling and cornification of the skin include all forms of psoriasis, e.g. psoriasis vulgaris, psoriasis pustulosa, psoriasis erythrodermica, psoriasis arthropathica, parapsoriasis, palmoplantar pustulosis, all forms of ichthyoses, e.g. ichthyosis vulgaris and congenital ichthyoses, keratodermias of all types, e.g., palmoplantar keratodermia, other genodermatoses with pathological cornification disorders, e.g. Darier's disease, further lichen ruber planus and pityriasis rubra pilaris.

In addition to psoriasis, other diseases or pathological conditions characterized by hyperproliferation and/or EGF-R overexpression and hyperactivity can be treated with the above-described compositions. These diseases and pathological conditions include, but are not limited to, keratinocyte proliferation and skin lesions caused or induced by Papilloma virus infection, seborrheic keratoses, acanthosis nigricans, ichthyosis (e.g. ichthyosis vulgaris and congenital ichthyoses), keratodermias, genodermatoses with pathological cornification disorders (e.g. Darier's disease), further lichen ruber planus, pityriasis rubra pilaris, and skin cancers such as basal cell carcinoma, squamous cell carcinoma and melanoma.

IV. Toxicity and Efficacy of Quinazoline Compounds

Toxicity and therapeutic efficacy of the above identified compounds can be determined by standard pharmaceutical procedures in cell cultures or experimental animals. A measure of the effectiveness and cell toxicity of a compound can be obtained by determining the therapeutic index: $LD_{50}/IC_{50}$. $IC_{50}$, the dose required to achieve 50% EGF-R tyrosine kinase activity inhibition, can be measured using standard techniques such as those described herein. $LD_{50}$, the dose lethal to 50% of the population, can be measured by standard techniques, such as using an MTT assay as described by Mossman, *J. Immunol. Methods* 65:55–63 (1983), by measuring the amount of LDH released as described by Korzeniewski and Callewaert, *J. Immunol. Methods* 64:313 (1983)and Decker and Lohmann-Matthes, *J. Immunol. Methods* 115:61 (1988), or by measuring the lethal dose in animal models. Another measure is the ratio $LD_{50}/ED_{50}$. $ED_{50}$ is the dose therapeutically effective in 50% of the population. Compounds which exhibit large therapeutic indices are preferred. The therapeutic index should be greater than 2, preferably at least 10, more preferably at least 50.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture.

Plasma half-life and biodistribution of the drug and metabolites in plasma and major organs can be determined to facilitate the selection of drugs most appropriate for the inhibition of a disorder. Such measurements can be carried out, for example, using HPLC analysis. Compounds that show potent inhibitory activity in the screening assays, but have poor pharmacokinetic characteristics, can be optimized by altering their chemical structure and retesting. In this regard, compounds displaying good pharmacokinetic characteristics can be used as models for the synthesis of other compounds.

Toxicity studies can also be carried out by measuring the blood cell composition. For example, toxicity studies can be carried out as follows: (1) the compound is administered to mice (an untreated control mouse should also be used); (2) blood samples are periodically obtained via the tail vein from one mouse in each treatment group; and 3) the samples are analyzed for red and white blood cells for indication of toxicity.

The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

Materials and Methods

Cells and Cell Culture. All tumor cell lines were obtained from the American Type Culture Collection (Rockville, Md.), unless otherwise specified. NIH3T3 mouse fibroblasts overexpressing the EGF receptor, IGF-1 receptor, insulin receptor, PDGF-b receptor, or a chimera of the EGF receptor extracellular domain fused to the Her-2 cytoplasmic domain were engineered using retroviral vectors. These cells will be referred to as 3T3-EGFR, 3T3-IGF1R, 3T3-IR, 3T3-PDGF-bR, and 3T3-EGFR/Her-2, respectively. All cell culture media and supplements were purchased from Gibco Life Technologies (Grand Island, N.Y.) unless otherwise specified. All cells were grown in a humid atmosphere of 90–95% air and 5–10% $CO_2$ at 37° C. Cell lines were maintained under standard conditions in culture media recommended by the ATCC, unless otherwise specified. 3T3-EGFR, 3T3-PDGF-bR, and 3T3-EGFR/Her-2 cells were maintained in DMEM containing 10% calf serum (CS) and 2 mM GLN. 3T3-IGF1R and 3T3-IR cells were maintained in DMEM containing 10% FBS and 2 mM GLN. Keratinocytes were obtained from small biopsy specimens of split-thickness skin from patients with psoriasis and from healthy control donors. The biopsy specimens were treated to yield a population of cells enriched for keratinocytes, which were maintained in keratinocyte growth medium as described (Ben-Bassat et al., *Exp. Dermatol.* 4:82–88, 1995).

In vitro functional studies. The effect of A1 on receptor phosphorylation, DNA replication, cell cycle progression, and cell growth was studied. Cell lines examined in receptor phosphorylation ELISA were 3T3-EGFR, 3T3-EGFR/Her-2, 3T3-PDGF-bR, 3T3-IGF1R, and 3T3-IR. For analysis of DNA replication (measured as incorporation of BrdU) and cell cycle progression, 3T3-EGFR and 3T3-PDGF-bR cell lines were used. Cell growth studies were carried out on A431 (EGF-R+), BT474 (Her-2+), and C6 (PDGF-bR+) cell lines. The effect of A1 on the growth of human psoriatic keratinocytes was determined as previously described (Ben-Bassat et al., *Exp. Dermatol.* 4:82–88, 1995).

Skin Penetration. In vitro skin penetration studies were conducted using human cadaver skin. The vehicle formulation consisted of a petrolatum based topical ointment containing 5.0% mineral oil, 3.0% glyceryl monostearate, 1.5% benzyl alcohol and 2.5% oleic acid. Six replicates of each A1 concentration (0.5%, 1.0%, 2.0% and 4.0% drug) were evaluated during each study. The formulations were spiked with radiolabeled $^{14}$C-A1 to obtain a specific radioactivity of 25 µCi/g. Radiolabeled $^{14}$C-A1 was provided by Synpep Corp, Alameda, Calif. (specific activity 5.89 mCi/mmol, lot #020196CL001). The formulation was applied (16.9 mg/cm$^2$) to human cadaver skin (1.77 cm$^2$ surface area and approximately 200 µm split thickness) mounted on a Franz static dffusion chamber. The chambers were filled with 4% BSA isotonic saline solution (6–10 mL reservoir volume) and equilibrated to a temperature of 37° C. by a circulating pump. Percent penetration through the skin was determined by measuring cumulative radioactivity in the reservoir medium at the end of 24 hours or at regular intervals during the 24 hour period. Tissue distribution of the drug in the stratum corneum, epidermis and dermis was determined at the end of 24 hours. The stratum corneum was separated by tape stripping with cellophane tape until "glistening". The dermis and epidermis were separated by microwave technique as described (Kumar et al., *Pharmaceutical Res.* 6:740–741, 1989; Bronaugh, "Preparation of biological membranes", In: *Methods for Skin Absorbtion,* pp 61–66. Ed. Barbara Kempanien and William G. Reifenrath, CRC Press, 1990).

EXAMPLE 1

Specific Inhibition of EGF-R Tyrosine Kinase Activity
EGF-R Whole Cell Kinase Assay NIH3T3 clone C7 engineered to over-express human EGF-R and the human glioblastoma line U1242 that expresses PDGFR-beta were used for cellular kinase assays.

The activity of the above identified compounds in inhibiting EGF-stimulated EGF-R phosphorylation was measured in an ELISA assay.

EGF-R kinase activity (EGF-R-3T3 assay) in whole cells was measured as described below:

A. Pre-coat ELISA Plate

Coat ELISA plates (Corning, 96 well, Cat. #25805-96) with 05-101 antibody at 0.5 $\mu$g per well in PBS, 150 $\mu$l final volume/well, and store overnight at 4° C. Coated plates are good for up to 10 days when stored at 4° C.

On day of use, remove coating buffer and replace with blocking buffer (5% Carnation Instant NonFat Dry Milk in PBS). Incubate the plate, shaking, at room temperature (about 23° C. to 25° C.) for 30 minutes. Just prior to use, remove blocking buffer and wash plate 4 times with TBST buffer.

B. Seeding Cells

EGF-R/C7 cell line was used for this assay.

Choose dishes having 80–90% confluence for the experiment. Trypsinize cells and stop reaction by adding 10% CS DMEM medium. Suspend cells in DMEM medium (10% calf serum (CS) DMEM medium) and centrifuge once at 1000 rpm, and once at room temperature for 5 minutes.

Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 $\mu$l per well, in a 96 well microtiter plate. Incubate seeded cells in 5% $CO_2$ at 37° C. for about 40 hours.

C. Assay Procedures

Check seeded cells for contamination using an inverted microscope. Dilute drug stock (10 mg/ml in DMSO) 1:10 in DMEM medium, then transfer 5 $\mu$l to a test well for a final drug dilution of 1:200 and a final DMSO concentration of 1%. Control wells receive DMSO alone. Incubate in 5% $CO_2$ at 37° C. for one hour.

Prepare EGF ligand: dilute stock EGF in DMEM so that upon transfer of 10 $\mu$l dilute EGF (1:12 dilution), 25 nM final concentration is attained.

Prepare fresh HNTG* sufficient for 100 $\mu$l per well; and place on ice.

| | |
|---|---|
| HNTG*: | 10 ml |
| HNTG stock (5x) | 2.0 ml |
| milli-Q $H_2O$ | 7.3 ml |
| EDTA, (100 mM, pH 7.0) | 0.5 ml |
| $Na_3VO_4$, (0.5 M) | 0.1 ml |
| $Na_4PO_7$, (0.2 M) | 0.1 ml |

After two hours of incubation with a drug, add prepared EGF ligand to cells, 10 $\mu$l per well, to yield a final concentration of 25 nM. Control wells receive DMEM alone. Incubate and shake at room temperature for 5 minutes.

Remove drug, EGF, and DMEM. Wash cells twice with PBS. Transfer HNTG* to cells, 100 $\mu$l per well. Place on ice for 5 minutes. Meanwhile, remove blocking buffer from other ELISA plate and wash with TBST as described above.

With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate and shake at room temperature for one hour.

Remove lysate and wash 4 times with TBST. Transfer freshly diluted anti-phosphotyrosine (anti-Ptyr) antibody to ELISA plate at 100 $\mu$l per well. Incubate shaking at room temperature for 30 minutes in the presence of the anti-Ptyr antiserum (1:3000 dilution in TBST).

Remove the anti-Ptyr antibody and wash 4 times with TBST. Transfer the freshly diluted TAGO 30 anti-rabbit IgG antibody (anti-rabbit IgG antibody: 1:3000 dilution in TBST) to the ELISA plate at 100 $\mu$l per well. Incubate shaking at room temperature for 30 minutes.

Remove detection antibody and wash 4 times with TBST. Transfer freshly prepared $ABTS/H_2O_2$ solution to ELISA plate, 100 $\mu$l per well. Incubate at room temperature for 20 minutes. $ABTS/H_2O_2$ solution: 1.2 $\mu$l 30% $H_2O_2$ in 10 ml ABTS stock.

Stop reaction by adding 50 $\mu$l 5N $H_2SO_4$ (optional), and determine O.D. at 410 nm.

The maximal phosphotyrosine signal is determined by subtracting the value of the negative controls from the positive controls. The percent inhibition of phosphotyrosine content for extract-containing wells is then calculated after subtraction of the negative controls.

D. Materials & Reagents

1) EGF Ligand: stock concentration=16.5 $\mu$M; EGF 201, TOYOBO, Co., Ltd. Japan.
2) 05-101 (UBI) (a monoclonal antibody recognizing an EGF-R extracellular domain).
3) Anti-Phosphotyrosine antibody (polyclonal) (made according to Fendley et al., *Cancer Research* 50:1550–1558, 1990).
4) TAGO antibody: Goat anti-rabbit IgG horse radish peroxidase conjugate, TAGO, Inc., Burlingame, Calif.

| | | |
|---|---|---|
| 5) | TBST buffer: | |
| | Tris-HCl, pH 7.2, | 50 nM |
| | NaCl, | 150 mM, |
| | Triton X-100 | 0.1% |
| 6) | HNTG 5X stock: | |
| | HEPES | 0.1 M |
| | NaCl | 0.75 M |
| | Glycerol | 50% |
| | Triton X-100 | 1.0% |
| 7) | ABTS stock: | |
| | Citric Acid | 100 rnM |
| | $Na_2HPO_4$ | 250 mM |
| | HCl, conc. | 4.0 pH |
| | ABTS* | 0.5 mg/ml |

*(2,2'-azinobis(3-ethylbenzthiazolinesulfonic acid). Keep solution in dark at 4° C. until use.

8) Stock reagents of:

| | |
|---|---|
| EDTA | 100 mM; pH 7.0 |
| $Na_3VO_4$ | 0.5 M |
| $Na_4PQ$ | 0.2 M |

Table 2 shows the activities of the quinazoline derivatives in the cellular EGF-R kinase assay and the ligand dependent cellular proliferation assay. Specifically, it shows the effectiveness of A1, A2, A3, A4, A6 and A5 in inhibiting EGF-R tyrosine kinase activity and curtailing EGF stimulated cell proliferation and the selectivity of the compounds. Table 2 shows $IC_{50}$ ($\mu M$) of the above identified compounds. $IC_{50}$ is the dose required to achieve 50% inhibition. In the order of decreasing activity, these compounds are A1, A4, A2, A3, A5 and A6.

To examine the effects of A1 on EGF-mediated receptor autophosphorylation, NIH 3T3 cells engineered to express EGF receptors (3T3-EGFR) were pretreated with titrated doses of A1 prior to the addition of ligand. ELISA analysis showed that EGF-stimulated receptor phosphorylation was decreased in a dose-dependent manner. The average $IC_{50}$ of six determinations was 13 nM.

To examine the effect of A1 on other receptor tyrosine kinases (RTK), NIH 3T3 cells engineered to overexpress various RTK were exposed to their corresponding ligands after pretreatment with A1, and the extent of ligand-stimulated receptor phosphorylation was determined by ELISA. As shown in Table 10, A1 inhibited receptor phosphorylation of the EGF receptor and a close relative, Her-2. However, other RTKs such as the platelet-derived growth factor receptor (PDGF-bR), the insulin-like growth factor receptor (IGF-1R) and the insulin receptor (IR) were not inhibited at concentrations up to 100 $\mu M$.

In Table 10, NIH 3T3 cells engineered to overexpress various RTKs were treated with corresponding ligand for 5 to 10 min following a 2 hr pretreatment with A1. Receptor phosphorylation was measured by ELISA. EGF-R/Her-2 denotes a chimeric receptor consisting of the extracellular (ligand-binding) domain of EGFR, and the transmembrane and cytoplasmic domains of Her-2.

EXAMPLE 2
Inhibition of NIH 3T3 Cells Overexpressing EGF-R
Cellular Growth Assay The efficacy of the above identified compounds in inhibiting or reducing EGF-R stimulated proliferation is measured by the 3T3 cell growth assay. The 3T3 growth assay was carried out as follows:

EGF-RC7 (NIH 3T3 C7 cells engineered to express EGF-R) and NIH 3T3C7 cells (as the control) were used for this assay. NIH3T3C7 cells were seeded at 2500 cells/well, 10 $\mu l$/well in 10% CS+2 mM Glutamine/DMEM, in a 96 well plate; EGF-RC7 cells were seeded at 6000 cells/well, 100 $\mu l$/well in 2% FBS+2 mM Glutamine/DMEM, in a 96 well plate. Cells were incubated at 37° C., 5% $CO_2$ overnight to allow for cell attachment to the plate.

A quinazoline compound was added to the cells at day 2. The compound was prepared in the appropriate growth medium (10% CS+2 mM glutamine in DMEM for NIH3T3C7 cells; 2% FBS+2 mM Glutamine in DMEM for EGF-RC7 cells) in a 96 well plate, and serially diluted. A total of 100 $\mu l$/well medium of the diluted compounds was added into the cells. The total volume of each well was 200 $\mu l$.

After the cells were treated with the compound for 4 days, the cells were washed with PBS and fixed with 200 $\mu l$/well ice-cold 10s TCA for one hour at 0–5° C.

Remove TCA and rinse wells 5 times with deionized water. Dry plates upside down with paper towels. Stain cells with 0.4% SRB at 100 $\mu l$/well for 10 minutes.

Pour off SRB and rinse plate 5 times with 1% acetic acid. Dry plate completely.

Solubilize the dye with 10 mM Tris-base at 100 $\mu l$/well for 10 minutes on a shaker.

Read the plate at dual wavelengths at 570 nm and 630 nm on Dynatech Elisa plate reader.

To determine whether the above identified compounds' inhibitory effect on EGF-R C7 cells is selective, the experiment described above was modified, replacing EGF-R C7 cells with human glioblastoma line U1242 that expresses PDGFR-beta.

The results of the assays described in Examples 1 and 2 are shown in Table 2. Example 1 demonstrates that the compounds of the invention are highly potent inhibitors of EGF-R enzymatic activity. Example 2 demonstrates that the compounds of the invention are also highly potent inhibitors of EGF-R mediated cellular proliferation and that they are highly selective as well. The most potent and most selective compound is A1.

Materials and Reagents
(1) Dulbecco's Modified Eagle Medium (D-MEM), Gibco 511965-050:
(2) Calf serum, Gibco 16170-029;
(3) Trypsin-EDTA, Gibco 25200-056;
(4) Fetal Bovine Serum Certified, Gibco 16000-028;
(5) Dulbecco'5 Phosphate-Buffered Saline (D-PBS), 10 Gibco 14190-029;
(6) Sulforhodamine B (SRB), Sigma 5-9012 0.4% SRB in 1% acetic acid;
(7) 10 mM Tris-base, Fisher BP152-5;
(8) 10% TCA, Trichroloacetic acid, Fisher A322-500;
(9) 96-well flat bottom plate (sterile), Corning 08-757-155;
(10) 100 ml reagent reservoir 9 (sterile), Matrix Technologies Corporation, 8086;
(11) Sterile pipet tips, Fisher 21-197-8E;
(12) 50 ml sterile TBST tubes, Fisher 05-539-6.

EXAMPLE 3
Toxicity Studies

The toxicity of each of the compounds of the invention was evaluated by determining the $LD_{10}$ and $LD_{50}$ (the dose lethal to 10% or 50% of a population) in mice.

Briefly, female BALB/c mice (5 per group) were injected with a single dose of compound 1P in 50 $\mu l$ DMSO. Survival was measured at seven days. The results are presented in Table 3 below and demonstrated that the compounds of the invention are relatively non-toxic.

Multiple dose toxicity studies were also conducted. A1 in DMSO was administered 1P to Balb/c nude mice at doses ranging from 5 to 30 mg/kg/day for 17, 20 or 30 days. The results are shown below:

| Exp | Dose | Duration | % Mortality |
|---|---|---|---|
| 1 | 30 | 17 | 0 |
| 2 | 5 | 20 | 0 |
| 3 | 10 | 20 | 0 |
| 4 | 30 | 20 | 0 |
| 3 | 30 | 33 | 25 |

Up to 12.5% mortality can periodically be observed with prolonged treatment (33 days) with vehicle control alone.

EXAMPLE 4
Skin Penetration and Absorption Studies

Three formulation categories (nine formulations total) consisting of Petrolatum Ointments, Emollient Creams and Polyethylene Glycol Ointments were developed for the skin penetration studies (Tables 6 and 7). The drug concentration was 2.0% for all formulations and time points were drawn at 0, 1 and 24 hours. There was an immediate turnaround of these results which indicated that the petrolatum ointments and the emollient creams showed approximately ten fold increase in penetration as compared to the PEG ointment with the percents listed in Tables 7 and 8.

Plasma levels of A1 were measured in nu/nu mice. Approximately 60 mg of a 2% (w/w/ointment was applied to the backs of four female mice using a stainless steel spatula. The dose was spread evenly over the back surface of each mouse.

Plasma was prepared from blood samples taken 30 or 60 min. following application (2 mice per time point) and examined by HPLC. In a second experiment, approximated 0.50 mg of the 2% (w/v) ointment was applied in the same manner. Blood samples were taken at 15 and 30 min and at 1, 2.25 and 30 hours. The mice exhibited no discomfort or increased grooming behavior for the duration of the experiments. Only trace (<2 µg/ml) amounts of A1 were detected at 30 min. or later time points. The lower limit of quantitation for the HPLC assay is 1.0 µg/ml.

Based on the above described studies, a topical formulation of A1 is prepared (see Table 9).

In another example, skin penetration studies were carried out using a petrolatum-based formulation containing 0.5, 1.0, 2.0 and 4.0 of A1. The results are summarized in Table 12. These data show that the amount of A1 recovered in the epidermis increased with the concentration applied to the skin and did not reach saturation at 4.0% A1. Furthermore, 0.5% A1 applied topically to human cadaver skin resulted in a concentration in the epidermis after 24 hours ranging from 141–355 µM. This is 10 to 25 fold more than the $IC_{99}$ for inhibition of psoriatic keratinocyte proliferation (by extrapolation of the growth inhibition curve, the $IC_{99}$ was estimated to be 14 µM on day 5). Thus, biologically relevant concentrations of the drug penetrated the skin and reached the target tissue (epidermis) within 24 hours of application.

Calculations to determine micromolar were made assuming that 100 microns of the skin section (200 microns total) represented epidermis. The area of the cadaver skin used was 1.77 $cm^2$. The calculated volume using this assumption is 17.7 µL. Molar concentration was calculated from the microgram recovery in the epidermis.

EXAMPLE 5
Inhibition of EGF-driven DNA Replication

Autophosphorylation of receptor tyrosine kinases such as the EGF-R initiates a signaling cascade that results in nuclear changes in the cell, including DNA replication and entry into the S-phase of the cell cycle. Therefore, the effect of A1 on ligand-induced DNA replication was studied. 3T3-EGFR cells and 3T3-PDGF-bR cells were stimulated with the corresponding ligand in the presence of titrated doses of A1. After 20 hours, DNA replication was determined by measuring the incorporation of bromodeoxyuridine (BrdU). EGF-driven DNA replication in 3T3-EGFR cells was significantly inhibited by A1 in a dose-dependent manner, with an $IC_{50}$ of 30 nM. In contrast, PDGF-driven DNA replication in 3T3-PDGF-bR cells was inhibited only by much higher concentrations of A1 ($IC_{50}$=10 µM).

EXAMPLE 6
A1 Inhibits EGF-driven Cell Cycle Progression

A1 was examined for its ability to inhibit receptor-stimulated cell cycle progression. 3T3-EGFR and 3T3-PDGF-bR cells were incubated with drug and ligand (EGF and PDGF, respectively) for 20 hours. The percentage of cells in various phases of the cell cycle was determined by propidium iodide staining and fluorescence activated cell sorting (FACS) analysis. Ligand stimulation of each cell line resulted in an increase in the percentage of cells in the S-phase (4% in resting cells, 52% in PDGF-stimulated, 72% in EGF-stimulated). Similar to the results seen in receptor phosphorylation and DNA synthesis assays, the addition of A1 inhibited cell cycle progression much more potently in the EGF-driven cells than in the PDGF-driven cells ($IC_{50}$= 34 nM [EGF], 4.1 µM [PDGF]). These data demonstrate that the inhibition of EGF-R autophosphorylation by A1 results in inhibition of downstream effects, suggesting that A1 might specifically inhibit EGF-driven cellular proliferation.

EXAMPLE 7
A1 Inhibits Cellular Proliferation Driven by the EGFR/Her Family of RTKs Since EGF receptor signaling and cell cycle progression were inhibited by A1, the effect of the compound on cellular proliferation was also examined. Cells expressing various receptor tyrosine kinases were seeded overnight in 10% FBS and A1 was added in titrated doses the next day. After 4 days, cell density was measured by SRB staining. $IC_{50}$ values were determined by regression analysis. For these experiments, cell lines whose growth is dependent on naturally-expressed RTK were examined. Cellular proliferation was measured by sulforhodamine B (SRB) staining after a 4 day incubation in the presence of titrated doses of A1, and $IC_{50}$ values were calculated. The data in Table 11 clearly show that A1 preferentially inhibited the growth of cell lines driven by the EGF-R/Her family of RTK, but did not inhibit PDGF-bR-dependent cell growth.

EXAMPLE 8
A1 Inhibits Growth of Psoriatic Human Keratinocytes

Keratinocytes were obtained from psoriasis patients after informed consent, and the effect of A1 on the growth of the keratinocytes was examined as described by Ben-Bassat et al., *Exp. Dermatol.* 4:82–88, 1995. A1 inhibited the growth of psoriatic keratinocytes, with an $IC_{50}$ of <1.0 µM on days 5 through 12 of culture. These results indicate that blocking EGF-R signaling is sufficient to inhibit the proliferation of psoriatic keratinocytes.

V. Formulations and Administration

The compounds of the present invention can be administered to a host alone, or in a pharmaceutical composition comprising the active compound and a carrier or excipient. The compounds also can be prepared as pharmaceutically acceptable salts. Examples of pharmaceutically acceptable salts include acid addition salts such as those containing hydrochloride, sulfate, phosphate, sulfamate, acetate, citrate, lactate, tartrate, methane sulfonate, ethane sulfonate, benzene sulfonate, p-toluene sulfonate, cyclohexylsulfamate and quinate (e.g. those disclosed in PCT/US92/03736 and PCT/GB94/01544, incorporated by reference herein). Such salts can be derived using acids such as hydrochloric acid, sulfuric acid, phosphoric acid, sulfamic acid, acetic acid, citric acid, lactic acid, tartaric acid, malonic acid, methane-sulfonic acid, ethanesulfonic acid, benzenesulfonic acid, p-toluenesulfonic acid, cyclohexylsulfamic acid, and quinic acid. Pharmaceutically acceptable salts also include alkali metal salts such as sodium or potassium salts, alkaline earth metal salts such as calcium or magnesium salts, ammonium salts or salts with an organic base which afford a physiologically-acceptable cation such as salts with methylamine, dimethylamine, trimethylamine, piperidine, morpholine or tris-(2-hydroxyethyl)amine.

Pharmaceutically acceptable salts can be prepared by standard techniques. For example, the free base form of the compound is first dissolved in a suitable solvent such as an aqueous or aqueous-alcohol solution containing the appropriate acid. The salt is then isolated by evaporating the solution. In another example, the salt is prepared by reacting the free base and acid in an organic solvent.

In accordance with this invention the aforementioned quinazoline derivatives can be administered to a subject for reducing or inhibiting keratinocyte proliferation. The compounds are useful as a prophylaxis or means for treating disorders such as psoriasis. The pharmaceutical compositions of the invention contain the compounds in association with a compatible pharmaceutically acceptable carrier material.

Techniques for formulation and administration may be found in *Remington's Pharmaceutical Sciences,* 18th ed., Mack Publishing Co., Easton, Pa. (1990). Any conventional carrier material can be utilized. The carrier material can be an organic or inorganic carrier material suitable for topical, enteral, percutaneous or parenteral administration. Carriers or excipients can be used to facilitate administration of the compound, for example, to increase the solubility of the compound. Suitable carriers and excipients include, but are not limited to, water, ethanol, polysorbate-80, triacetin, gelatin, gum arabic, lactose, starch, magnesium stearate, talc, vegetable oils, polyalkyleneglycols, petroleum jelly, benzyl alcohol, polyethylene glycols (e.g. PEG-300 and PEG-400), propylene carbonate, propylene glycol, Transcutol, Petrolatum, vegetable oils, mineral oil, stearyl alcohol, Laureth-4, calcium carbonate, calcium phosphate, various sugars or types of starch, cellulose derivatives and mixtures thereof. Furthermore, the pharmaceutical preparations may contain other pharmaceutically active agents. Additional additives such as flavoring agents, preservatives, stabilizers, emulsifying agents, buffers and the like may be added in accordance with accepted practices of pharmaceutical compounding.

Table 4 lists the excipients used for solubility testing of A1. The amount of compound for each test was between 1 to 15 mg/mL unless otherwise indicated. Visual solution clarity was recorded immediately and 24 Hrs. after rocking at room temperature in a type I glass container. Table 5 shows the solubility of A1 in more excipients.

The pharmaceutical preparations can be made up in any conventional form including: (a) a solid form for oral administration such as tablets, capsules, pills, powders, granules, and the like; (b) a liquid form for oral administration such as solutions, syrups, suspensions, elixirs and the like; (c) preparations for parenteral administration such as sterile solutions, suspensions or emulsions; and (d) preparations for topical administrations such as solutions, suspensions, ointments, creams, gels, micronized powders, aerosols, aqueous gels, Petrolatum ointments, PEG ointments and the like. The pharmaceutical preparations may be sterilized and/or may contain adjuvants such as preservatives, stabilizers, wetting agents, emulsifiers, salts for varying the osmotic pressure and/or buffers.

For topical administration to the skin the aforementioned compounds are preferably prepared as ointments, tinctures, creams, gels, solutions, lotions, sprays, suspensions, shampoos, hair soaps, perfumes and the like. In fact, any conventional composition utilized for application to the scalp or skin can be utilized in accordance with this invention. Preferred formulations include gels, lotions and creams. The pharmaceutical preparation for topical administration to the skin can be prepared by mixing the aforementioned active ingredient (i.e., a pharmaceutically effective amount of a compound) with non-toxic, therapeutically inert, solid or liquid carriers customarily used in such preparations.

In preferred embodiments, these preparations contain at least about 0.0005 percent by weight, of the active ingredient based upon the total weight of the composition. The active ingredient, the compound, may be used in topical compositions in amounts significantly exceeding 10 percent. It is preferred that these preparations contain about 0.01 to 10 percent by weight of the active ingredient based upon the total weight of the composition.

It is also preferred that these preparations are applied once or twice daily to the skin. These preparations can be applied according to the need of the patient. In carrying out this invention, the active ingredient can be applied in an aqueous solution or an alcohol solution such as ethyl alcohol.

In preparing the topical preparations described above additives such as preservatives, thickeners, perfumes and the like conventional in the art of pharmaceutical compounding can be used. In addition, conventional antioxidants or mixtures of conventional antioxidants can be incorporated into the topical preparations containing the aforementioned active agent. Among the conventional antioxidants which can be utilized in these preparations are included N-methyl-α-tocopherolamine, tocopherols, butylated hydroxyanisole, butylatedhydroxytoluene, ethoxyquin and the like. Cream-base pharmaceutical formulations containing the active agent, used in accordance with this invention, are composed of aqueous emulsions containing a fatty acid alcohol, semi-solid petroleum hydrocarbon, 1,2-ethyleneglycol and an emulsifying agent.

Ointment formulations containing the active agent in accordance with this invention comprise admixtures of a semi-solid petroleum hydrocarbon with a solvent dispersion of the active material. Cream compositions containing the active ingredient for use in this invention preferably comprise emulsions formed from a water phase of a humectant, a viscosity stabilizer and water, an oil phase of fatty acid alcohol, a semisolid petroleum hydrocarbon and an emulsifying agent and a phase containing the active agent dispersed in an aqueous stabilizer-buffer solution. Stabilizers may be added to the topical preparation. Any conventional stabilizer can be utilized in accordance with this invention. In the oil phase, fatty acid alcohol components function as a stabilizer. These fatty acid alcohol components are derived from the reduction of a long-chain saturated fatty acid at least about 14 carbon atoms. Also, conventional perfumes and lotions generally utilized in topical preparation for the hair can be utilized in accordance with this invention. Furthermore, if desired, conventional emulsifying agents can be utilized in the topical preparations of this invention.

Parenteral dosage forms can be infusions or injectable solutions. Such dosage forms can be injected, e.g., intravenously, subcutaneously or intramuscularly. These preparations can also contain other medicinally active substances. In preferred embodiments, a daily dosage of from about 0.01 mg to about 2 mg per Kg of body weight is utilized in parenteral formulations. In further preferred embodiments, a daily dosage of from about 0.025 mg to about 0.5 mg per kg of body weight of the patient is utilized. Additional additives such as flavoring agents, preservatives, stabilizers, emulsifying agents, buffers and the like may be added in accordance with accepted practices of pharmaceutical compounding.

A preferred oral dosage form comprises capsules of hard or soft gelatin methylcellulose or of another suitable material easily dissolved in the digestive tract. The enteral dosages contemplated in accordance with the present invention will vary in accordance with the needs of the individual patient as determined by the prescribing physician. In preferred embodiments a daily dosage of from about 0.01 mg. to about 2 mg per Kg of body weight is utilized. In further preferred embodiments a daily dosage of from about 0.025 mg to about 0.5 mg per kg of body weight of the patient is utilized. This dosage may be administered according to any dosage schedule determined by the physician in accordance with the requirements of the patient.

It is likewise within the purview of the present invention to incorporate the therapeutically active substances enumerated herein in any desired amount for enteral administration within the oral unit dosage form. It is preferred, however, to formulate preparations containing the active substance of the present invention in such a manner that each dose contains from about 0.05 mg to about 100 mg, particularly from about 0.1 mg to about 10 mg of the active substance with suitable therapeutically inert fillers and diluents. It is especially preferred to incorporate such a dosage into soft gelatin capsules and tablets.

All publications referenced are incorporated by reference herein, including the nucleic acid sequences and amino acid sequences listed in each publication. All the compounds disclosed and referred to in the publications mentioned above are incorporated by reference herein, including those compounds disclosed and referred to in articles cited by the publications mentioned above.

Other embodiments of this invention are disclosed in the following claims.

TABLE 1

Structures of Quinazoline Compounds

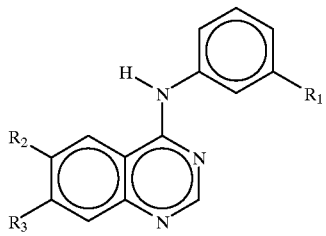

| Compound | $X_1$ | $X_2$ | $X_3$ |
|---|---|---|---|
| A1 | Br | methoxy | methoxy |
| A2 | Cl | methoxy | methoxy |
| A3 | Cl | methyl | H |
| A4 | $CF_3$ | methoxy | methoxy |
| A5 | CN | methoxy | methoxy |
| A6 | $CF_3$ | methyl | H |

TABLE 2

Inhibition of EGF-R Tyrosine Kinase Activity and Cellular Growth by Quinazoline derivatives

| Compound | EGFR Kinase IC50 ($\mu$M) | 3T3-EGFR IC50 ($\mu$M) | 3T3-PDGFR IC50 ($\mu$M) | PDGFR/ EGFR IC50/IC50 |
|---|---|---|---|---|
| A4 free base | <0.006 | 0.4 | 28 | 70 |
| A1 free base | 0.0009 | 0.075 | 15 | 200 |
| A2 free base | <0.015 | 0.11 | 18 | 163 |
| A6 free base | 0.9 | 6.0 | 30 | 5 |
| A3 free base | 0.058 | 2.0 | 10 | 5 |
| A5 free base | 0.2 | 1.5 | >100 | 67 |

TABLE 3

Toxicity of Quinazoline Compounds (mg/kg)

| | Toxicity* (mg/kg) | | Plasma Concentration** ($\mu$g/mL) | | |
|---|---|---|---|---|---|
| | $LD_{10}$ | $LD_{50}$ | 5 min | 15 min | 60 min |
| A3 | $LD_{20}$ =400 | >400 | 7.87 ± 0.98 | 3.43 ± 0.82 | 1.34 ± 0.11 |
| A2 | >200 no deaths | >200 no deaths | 11.5 ± 4.0 | 6.5 ± 1.3 | 3.7 ± 0.5 |
| A6 | >400 no deaths | >400 no deaths | 4.45 ± 1.38 | 2.01 ± 0.53 | 0.54 ± 0.2 |
| A1 | 75 | ~300 | 17.9 ± 4.3 | 6.3 ± 3.7 | 2.0 ± 0.9 |
| A4 | $LD_{40}$ = 400 | $LD_{40}$ = 400 | 13.3 ± 1.5 | 12.7 ± 3.0 | 3.9 ± 1.5 |
| A5 | >153 no deaths | >153 no deaths | 0.95 ± 0.42 | 0.65 ± 0.19 | 0.13 ± 0.06 |

*Single dose, IP, in BALB/c, female mice.
**Single dose (50 mg/kg), IP, in BALB/c, nu/nu, female mice.

TABLE 4

EXCIPIENT SCREENING FOR A1

| Excipient | Excipient Ratio | [Drug] (mg/mL) | Solubility After 24 Hrs. |
|---|---|---|---|
| Distilled $H_2O$ | | | Insoluble |
| 1.0 N HCl | | | Insoluble/Yellow discoloration |
| Conc. NaOH | | | Insoluble |
| Ethanol | | | Partially Soluble |
| Polysorbate-80 | | 10 | Slightly Soluble |
| EtOH/Poly-80 | 50:50 | 10 | Slightly Soluble |
| Benzyl Alcohol | | | Soluble |
| Triacetin | | | Partially Soluble |
| Oleic Acid | | | Insoluble/Yellow/Cloudy |
| Isopropyl Myristate | | | Insoluble/Cloudy |
| PEG-300 | | | Soluble |
| Propylene Glycol | | | Slightly Soluble/Clear/ Particulates |
| Propylene Carbonate | | | Soluble/80C/10 min. |

TABLE 5

SOLUBILITY OF A1 IN PURE SOLVENTS

| | Soluble at (% w/w) | Not Soluble at (% w/w) |
|---|---|---|
| Compendial Excipients | | |
| Benzyl Alcohol, NF | 3.60 | 4.77 |
| Betizyl Berizoate, USP | | 0.85 |
| Dehydrated Alcohol, USP | 0.76 | 0.98 |
| Isopropyl Alcohol, 99%, usp | — | 1.25 |
| Octyldodecanol, NF | | 0.68 |
| Oleic Acid, NF | | 1.00 |
| Polyethylene Glycol 300, USP | 1.00 | 2.10 |
| Polyethylene Glycol 400, USP | 1.76 | 2.44 |
| Polysorbate 20, NF | | 0.99 |
| Propylene Carbonate, NF | 0.98 | 1.46 |
| Propylene Glycol, USP | | 0.59 |
| Triacetin USP | | 0.96 |
| Non-Compendial Excipients | | |
| Caprylic/Capric Triglyceride (Miglyol 812) | | 0.84 |
| Diethyl Sebacate not compatible (yellow) | | |
| Diisopropyl Adipate | | 0.66 |
| Dimethyl isosorbide | | 0.97 |

TABLE 5-continued

SOLUBILITY OF A1 IN PURE SOLVENTS

|  | Soluble at (% w/w) | Not Soluble at (% w/w) |
|---|---|---|
| Ethoxydiglycol (Transcutol) | 2.41 | 3.74 |
| Finsolve TN (Finetex) |  | 1.27 |
| Hexylene Glycol | 0.98 | 2.05 |
| Isotearyl Alcohol |  | 0.99 |
| Laureth 4 | 4.10 | — |

TABLE 6

A1 FORMULATIONS FOR SKIN PENETRATION STUDIES

| Formulation Category | Drug Form | Major Excipients |
|---|---|---|
| 1. Aqueous Gels | Solution | Water, PEG 400, Transcutol, propylene glycol, benzyl alcohol |
| 2. Petrolatum Ointment | Solution | Petrolatum, propylene carbonate |
| 3. PEG Ointments | Solution | PEG 400, benzyl alcohol, Laureth-4, Transcutol |
| 4. Creams | Suspended | Aqueous phase: propylene glycol, water, surfactants, Oil phase: mineral oil, stearyl alcohol. |

Drug Concentration: 2% w/w in all the formulations (except aqueous gels)

TABLE 7

SUMMARY RESULTS A1 PENETRATION STUDY

| | Polyethylene Glycol Ointments | | | |
|---|---|---|---|---|
| Excipients | SG-94A A | SG-89A B | SG-90A C | SG-91A D |
| Polyethylene Glycol 400, NF | 71.0 | 64.0 | 64.0 | 58.5 |
| Benzyl Alcohol, NF | 3.0 | ***** | ***** | 2.0 |
| Laureth 4 | ***** | ***** | ***** | 2.5 |
| White Petrolatum, USP | ***** | ***** | ***** | ***** |
| Propylene Carbonate, NF | ***** | ***** | 10.0 | ***** |
| Propylene Glycol, USP | ***** | 10.0 | ***** | 10.0 |
| Polyethylene Glycol 3350, NF | 24.0 | 24.0 | 24.0 | 25.0 |
| A1 | 2.0 | 2.0 | 2.0 | 2.0 |
| Penetration Results | | | | |
| μg Penetrated (R + D + E)* | 1.8 | 1.6 | 1.9 | 3.2 |
| μg Penetrated (R + D + E + SC)** | 3.0 | 2.7 | 2.9 | 6.5 |
| Percent of Dose (R + D + E) | 0.3 | 0.3 | 0.3 | 0.5 |

| | Petrolatum Ointments | |
|---|---|---|
| Excipients | SG-92A E | SG-93A F |
| White Petrolatum, USP | 83.5 | 82.5 |
| Benzyl Alcohol, NF | 1.5 | ***** |
| Lt. Mineral Oil, NF | 5.0 | ***** |
| White Wax, NF | ***** | 5.0 |
| Propylene Carbonate, NF | ***** | 7.5 |
| White Wax, NF | ***** | 5.0 |
| Glyceryl Monostearate, NF | 3.0 | 3.0 |
| A1 | 2.0 | 2.0 |
| Oleic Acid, NF | 5.0 | ***** |
| Penetration Results | | |
| μg Penetrated (R + D + E)* | 34.4 | 21.3 |
| μg Penetrated (R + D + E + SC)** | 47.2 | 33.6 |
| Percent of Dose (R + D + E) | 5.7 | 3.6 |

| | Emollient Creams | | |
|---|---|---|---|
| Excipients | SG-98A G | SG-98B H | SG-99A I |
| Stearyl Alcohol, USP | 10.0 | 10.0 | 6.0 |
| Cetyl Alcohol, USP | ***** | ***** | 0.5 |
| White Petrolatum, USP | 5.0 | 5.0 | ***** |
| Octyldodecanol, NF | 5.0 | 5.0 | 5.0 |
| Sorbitan Monostearate, NF | ***** | ***** | 1.0 |
| Polyoxyl 40 Stearate, NF | ***** | ***** | 4.0 |
| Brij 721 | 2.0 | 2.0 | ***** |
| Brij 72 | 2.4 | 2.4 | ***** |
| Purified Water, USP | 58.1 | 66.1 | 60.8 |
| Propylene Glycol, USP | 5.0 | 5.0 | 20.0 |
| Benzyl Alcohol, NF | ***** | 2.0 | ***** |
| Ethoxydiglycol [Transcutol] | 10.0 | ***** | ***** |
| Methylparaben, USP | 0.2 | 0.2 | 0.2 |
| 10% NaOH Solution | ***** | ***** | 0.2 |
| Carbopol 980, NF | ***** | ***** | 0.3 |
| Hydroxyethyl Cellulose 250HHX | 0.3 | 0.3 | ***** |
| A1 | 2.0 | 2.0 | 2.0 |
| Penetration Results | | | |
| μg Penetrated (R + D + E)* | 16.5 | 20.7 | 14.8 |
| μg Penetrated (R + D + E + SC)** | 22.7 | 27.1 | 21.0 |
| Percent of Dose (R + D + E) | 2.8 | 3.4 | 2.5 |

*R + D + E = Reservoir + Dermis + Epidermis
**R + D + E + SC = Reservoir + Dermis = Epidermis + Stratum Corneum

TABLE 8

SKIN PENETRATION STUDIES

| Formulation Category | No. of Formulations | Drug Form (2% w/w) | Major Excipients | Percent Skin Penetration* |
|---|---|---|---|---|
| Petrolatum Ointment | 2 | Suspended | White Petrolatum (84%), oleic acid, propylene carb., benzyl alcohol | 3.6–5.7 |
| Creams | 3 | Suspended | Water (60%), surfactant, alcohol propylene carb., mineral oil | 2.5–3.4 |
| Polyethylene Glycol Ointment | 4 | Dissolved | PEG-400 (58–71%) benzyl alcohol, laureth-4, transcutol | 0.3–0.5 |

TABLE 9

A1 TOPICAL FORMULATION

| FORMULATION DESIGNATION | PERCENT CONC. (w/w) |
|---|---|
| A1 | 1.0. or 4.0% |
| Mineral Oil, NF | 5.00% |
| Glyceryl Monostearate, NF | 3.00% |
| Benzyl Alcohol, NF | 0.75% |
| Oleic Acid, NF | 2.50% |
| Butylated Hydroxytoluene | 0.001% |
| White Petrolatum, USP | QS to 100% |

TABLE 10

Selectivity of A1

| RECEPTOR | LIGAND | IC$_{50}$ ($\mu$M) |
|---|---|---|
| EGF-R | EGF | 0.02 |
| EGF-R/Her-2 | EGF | 0.60 |
| PDGF-bR | PDGF | >100 |
| IGF-1R | IGF-1 | >100 |
| IR | Insulin | >100 |

TABLE 11

Effect of A1 on cell growth

| CELL LINE | RTK | IC$_{50}$ ($\mu$M) |
|---|---|---|
| A431 | EGF-R | 1.6 |
| BT474 | Her-2 | 0.9 |
| C6 | PDGF-bR | >100 |

TABLE 12

Skin penetration studies: recovery of A1 in the epidermis

| Percent A1 | Epidermis $\mu$g Recovery | Epidermis $\mu$M Concentration |
|---|---|---|
| 0.5 | 1.6 ± 0.7 | 248 ± 107 |
| 1.0 | 2.3 ± 1.0 | 355 ± 151 |
| 2.0 | 4.5 ± 1.0 | 712 ± 157 |
| 4.0 | 16.3 ± 9.4 | 2561 ± 1469 |

We claim:

1. A method for treating a hyperproliferative skin disorder in a host, comprising the step of administering to said host a composition containing a pharmaceutically effective amount of a compound selected from the group consisting of 4-(3-Bromophenylamino)-6,7-dimethoxyquinazoline, 4-(3-Chlorophenylamino)-6,7-dimethoxyquinazoline, 4-(3-Chlorophenylamino)-6,-methoxyquinazoline, 4-[3-(triflouromethyl)phenylamino]-6,7-dimethoxyquinazoline, 4-(3-Cyanophenylamino)-6,7-dimethoxyquinazoline, 4-[3-(triflouromethyl)phenylamino]-6-methylquinazoline, and a pharmaceutically acceptable salt therof, wherein said hyperproliferative skin disease is selected from the group consisting of psoriasis and hyperproliferation caused by papilloma virus infection.

2. The method according to claim 1 wherein said composition is administered to said host by topical application.

3. The method according to claim 1 wherein said compound is 4-(3-Bromophenylamino)-6,7-dimethoxyquinazoline or a pharmaceutically acceptable salt thereof.

4. The method according to claim 1 wherein said composition comprises a pharmaceutically acceptable carrier.

5. A method for reducing skin lesions caused by Papilloma virus infection in a host, comprising the step of administering to said host a composition containing a pharmaceutically effective amount of a compound selected from the group consisting of 4-(3-Bromophenylamino)-6,7-dimethoxyquinazoline, 4-(3-Chlorophenylamino)-6,7-dimethoxyquinazoline, 4-(3-Chlorophenylamino)-6-methylquinazoline, 4-[3-(trifluoromethyl)phenylamino]-6,7-dimethoxyquinazoline, 4-(3-Cyanophenylamino)-6,7-dimethoxyquinazoline, 4-[3-(trifluoromethyl)phenylamino]-6-methylquinazoline, and a pharmaceutically acceptable salt thereof.

6. A method for treating psoriasis in a host, comprising the step of administering to said host a composition containing a pharmaceutically effective amount of a compound selected from the group consisting of 4-(3-Bromophenylamino)-6,7-dimethoxyquinazoline, 4-(3-Chlorophenylamino)-6,7-dimethoxyquinazoline, 4-(3-Chlorophenylamino)-6-methylquinazoline, 4-[3-(trifluoromethyl)phenylamino]-6,7-dimethoxyquinazoline, 4-(3-Cyanophenylamino)-6,7-dimethoxyquinazoline, 4-[3-(trifluoromethyl)phenylamino]-6-methylquinazoline, and a pharmaceutically acceptable salt thereof.

7. The method according to claim 1, wherein said compound is 4-(3-Bromophenylamino)-6,7-dimethoxyquinazoline.

8. The method according to claim 5 or 6, wherein said compound is 4-(3-Bromophenylamino)-6,7-dimethoxyquinazoline.

* * * * *